US010170275B2

(12) United States Patent
Mitchels et al.

(10) Patent No.: US 10,170,275 B2
(45) Date of Patent: Jan. 1, 2019

(54) CRYOGENIC SPECIMEN PROCESSING IN A CHARGED PARTICLE MICROSCOPE

(71) Applicant: FEI Company, Hillsboro, OR (US)

(72) Inventors: John Mitchels, Brno (CZ); Tomáš Vystavěl, Brno (CZ); Martin Cafourek, Třebíč (CZ)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/787,352

(22) Filed: Oct. 18, 2017

(65) Prior Publication Data

US 2018/0114671 A1   Apr. 26, 2018

(30) Foreign Application Priority Data

Oct. 20, 2016  (EP) .................................. 16194724

(51) Int. Cl.
*H01J 37/256*  (2006.01)
*H01J 37/18*  (2006.01)
*H01J 37/20*  (2006.01)
*H01J 37/26*  (2006.01)
*G01N 1/42*  (2006.01)

(52) U.S. Cl.
CPC .............. *H01J 37/261* (2013.01); *G01N 1/42* (2013.01); *H01J 37/18* (2013.01); *H01J 37/185* (2013.01); *H01J 37/20* (2013.01); *H01J 2237/022* (2013.01); *H01J 2237/2001* (2013.01); *H01J 2237/2602* (2013.01); *H01J 2237/28* (2013.01); *H01J 2237/317* (2013.01)

(58) Field of Classification Search
CPC .......... H01J 37/18; H01J 37/20; H01J 37/261; H01J 2237/2001; H01J 2237/2602
See application file for complete search history.

(56) References Cited

U.S. PATENT DOCUMENTS 5,093,577 A    3/1992  de Poorter et al.
5,885,402 A *  3/1999  Esquibel ........... H01J 37/32935
                                              156/345.24
(Continued)

FOREIGN PATENT DOCUMENTS

JP    2011034741    2/2011

OTHER PUBLICATIONS

Extended European Search Report mailed by the European Patent Office dated May 4, 2017, for EP App. No. 16194724.7.

*Primary Examiner* — Nicole Ippolito
*Assistant Examiner* — Sean Luck
(74) *Attorney, Agent, or Firm* — Klarquist Sparkman, LLP

(57) ABSTRACT

Surface modification of a cryogenic specimen can be obtained using a charged particle microscope. A specimen is situated in a vacuum chamber on a specimen holder and maintained at a cryogenic temperature. The vacuum chamber is evacuated and a charged-particle beam is directed to a portion of the specimen so as to modify a surface thereof. A thin film monitor is situated in the vacuum chamber and has at least a detection surface maintained at a cryogenic temperature. A precipitation rate of frozen condensate in the vacuum chamber is measured using the thin film monitor, and based on the measured precipitation rate, the surface modification is initiated when the precipitation rate is less than a first pre-defined threshold, or interrupted if the precipitation rate rises above a second pre-defined threshold.

20 Claims, 2 Drawing Sheets

(56) References Cited

U.S. PATENT DOCUMENTS

| | | | |
|---|---|---|---|
| 6,552,340 B1 * | 4/2003 | Krivanek | H01J 37/153 250/305 |
| 2007/0187601 A1 | 8/2007 | Mito et al. | |
| 2007/0262050 A1 | 11/2007 | Golovchenko et al. | |
| 2008/0063810 A1 * | 3/2008 | Park | C23C 16/4401 427/569 |
| 2010/0108882 A1 * | 5/2010 | Zewail | H01J 37/22 250/307 |
| 2010/0327180 A1 * | 12/2010 | Schwind | H01J 37/05 250/396 R |

* cited by examiner

CRYOGENIC SPECIMEN PROCESSING IN A CHARGED PARTICLE MICROSCOPE

CROSS REFERENCE TO RELATED APPLICATION

This application claims priority to European Patent Application No. 16194724.7, filed Oct. 20, 2016, which is incorporated herein by reference.

BACKGROUND

Charged-particle microscopy is a well-known and increasingly important technique for imaging microscopic objects, particularly in the form of electron microscopy. Historically, the basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example.

More specifically, in a SEM, irradiation of a specimen by a scanning electron beam precipitates emanation of "auxiliary" radiation from the specimen, in the form of secondary electrons, backscattered electrons, X-rays and cathodoluminescence (infrared, visible and/or ultraviolet photons), for example; one or more components of this emanating radiation is/are then detected and used for image accumulation purposes. In a TEM, the electron beam used to irradiate the specimen is chosen to be of a high-enough energy to penetrate the specimen (which, to this end, will generally be thinner than in the case of a SEM specimen); the transmitted electrons emanating from the specimen can then be used to create an image. When such a TEM is operated in scanning mode (thus becoming a STEM), the image in question will be accumulated during a scanning motion of the irradiating electron beam. More information on some of the topics elucidated here can be found in the WIKIPEDIA entries "Electron Microscope," "Scanning Electron Microscope," "Transmission Electron Microscopy," and "Scanning Transmission Electron Microscopy."

As an alternative to the use of electrons as irradiating beam, charged particle microscopy can also be performed using other species of charged particle. In this respect, the phrase "charged particle" should be broadly interpreted as encompassing electrons, positive ions (e.g. Ga or He ions), negative ions, protons and positrons, for instance. As regards non-electron-based charged particle microscopy, some further information can, for example, be gleaned from references such as the WIKIPEDIA entries "Focused Ion Beam" and "Scanning Helium Ion Microscope," Escovitz et al., "Scanning Transmission Ion Microscope with a Field Ion Source", Proc. Nat. Acad. Sci. USA 72(5), pp 1826-1828 (1975), and Varentsov et al., "First Biological Images with High-Energy Proton Microscopy," available from the PUBMED Database.

It should be noted that, in addition to imaging and performing (localized) surface modification (e.g. milling, etching, deposition, etc.), a charged particle microscope may also have other functionalities, such as performing spectroscopy, examining diffractograms, etc.

A Charged-Particle Microscope (CPM) generally comprises at least the following components: (i) a vacuum chamber, connected to one or more vacuum pumps and containing one or more ports (e.g. load locks) for moving (individual and/or groups of) specimens into and out of the vacuum chamber, (ii) particle-optical column comprising a radiation source, such as a Schottky electron source or ion gun, and an illuminator, which serves to manipulate a "raw" radiation beam from the source and perform upon it certain operations such as focusing, aberration mitigation, cropping (with an aperture), filtering, etc. It will generally comprise one or more (charged-particle) lenses, and may comprise other types of (particle-)optical component also. If desired, the illuminator can be provided with a deflector system that can be invoked to cause its exit beam to perform a scanning motion across the specimen being investigated. (iii) A specimen holder, on which a specimen under investigation can be held and positioned (e.g. tilted, rotated). If desired, this holder can be moved so as to effect scanning motion of the specimen w.r.t. the beam. In general, such a specimen holder will be connected to a positioning system. When designed to hold cryogenic specimens, the specimen holder will comprise means for maintaining said specimen at cryogenic temperatures, e.g. using an appropriately connected cryogen vat. (iv) A detector (for detecting radiation emanating from an irradiated specimen), which may be unitary or compound/distributed in nature, and which can take many different forms, depending on the radiation being detected. Examples include photodiodes, CMOS detectors, CCD detectors, photovoltaic cells, X-ray detectors (such as Silicon Drift Detectors and Si(Li) detectors), etc. In general, a CPM may comprise several different types of detector, selections of which can be invoked in different situations.

In the particular case of a dual-beam microscope, there will be (at least) two particle-optical columns, for producing two different species of charged particle. Commonly, an electron column (arranged vertically) will be used to image the specimen, and an ion column (arranged at an angle) will be used to (concurrently) modify (machine/process) the specimen, whereby the specimen holder can be positioned in multiple degrees of freedom so as to suitably "present" a surface of the specimen to the employed electron/ion beams.

In the case of a transmission-type microscope (such as a (S)TEM, for example), a CPM will specifically comprise an imaging system, which essentially takes charged particles that are transmitted through a specimen (plane) and directs (focuses) them onto analysis apparatus, such as a detection/imaging device, spectroscopic apparatus (such as an EELS device), etc. As with the illuminator referred to above, the imaging system may also perform other functions, such as aberration mitigation, cropping, filtering, etc., and it will generally comprise one or more charged-particle lenses and/or other types of particle-optical components.

As already mentioned, an example of an apparatus as set forth in the opening paragraph above is a FIB-SEM, and an important (but non-limiting) example of the use of such an apparatus is in the preparation of so-called TEM lamellae. As indicated above, TEM specimens need to be very thin, and they are generally prepared using highly specialized techniques. In one such technique, a focused ion beam (FIB) is used to cut/slice/extricate one or more lamella/lamellae from a bulk specimen, whereby, in general, electron-beam imaging is used to find/position a particular zone of interest on a specimen that is mounted to the specimen holder, the FIB is used to perform various incisions necessary to liberate a lamella from the (identified zone of the) specimen, and the lamella thus differentiated from the rest of the specimen is picked up/moved using a needle-like manipulator, attached to a positioning stage.

Lamella produced in this manner can then be removed from the FIB-SEM (with the aid of said manipulator), and studied in a (S)TEM, or in other analysis apparatus. For some general information on TEM lamella preparation, see, for example, Muehle et al. in "Microscopy: Science, Technology, Applications and Education," pp. 1704-1716, 2010 (Formatex). For more information on the use of a FIB-SEM to prepare specimens for life sciences studies, see, for example, Rigort et al., "Cryo-focused-ion-beam Applications in Structural Biology," available online from the PUBMED Database. Both of these publications are incorporated herein by reference.

The preparation of such TEM lamella is generally challenging, but is particularly challenging in the case of cryogenic specimens. Typical examples of cryogenic specimens include biological samples (such as cells, cell components, single-cellular organisms, etc.), which, by their very nature, typically need to be stored and studied in a body of aqueous liquid (such as water, electrolyte, cell fluid, blood plasma, etc.). Since an aqueous liquid introduced into a (quasi-) vacuum environment of a CPM will start to outgas/boil, the specimen (sample and aqueous liquid) is first frozen before being exposed to vacuum. Typically, so as to prevent damage to the sample caused by the formation of (sharp) ice crystals, such freezing is performed very rapidly, with the aim of achieving sample vitrification (solidification into an amorphous, glass-like phase) without significant ice crystallization; such vitrification can, for example, be achieved by rapidly plunging a specimen into a bath of cryogen, e.g. as set forth in U.S. Pat. No. 9,116,091 and European Patent 2 853 847 (with the same assignee as the current disclosure).

When a cold body is introduced into a vapor-containing (e.g. partially humid) environment, vapor in that environment will tend to condense on the cold body. If the body is sufficiently cold, the condensate in question will form as a layer of frozen/congealed solid, e.g. water ice. In a CPM, this is generally highly undesirable, since ice (or other condensate material) on a specimen surface will tend to absorb/scatter/deform a charged-particle beam directed onto that surface and crystalline ice on a biological sample surface may cause irreparable damage to that surface.

As a result, when cryogenic specimens are introduced into a CPM vacuum chamber from a load port (e.g. a load lock, access door to a storage space, etc.), the vacuum chamber must be subjected to a (fresh, continuing, or supplementary) lengthy pump-down so as to ensure that any vapor that is inadvertently co-introduced with the specimen is thoroughly removed from its environment; in this way, one seeks to ensure that, once surface modification of the specimen begins, there will be no build-up of condensate on the freshly modified surface. This is a time-consuming operation that can introduce a considerable throughput penalty in a process workflow.

SUMMARY

In what follows, the disclosure may—by way of example—sometimes be set forth in the specific context of electron microscopy; however, such simplification is intended solely for clarity/illustrative purposes, and should not be interpreted as limiting.

The disclosure relates to a method of performing surface modification of a cryogenic specimen using a charged particle microscope comprising a vacuum chamber, with a port for loading the specimen into the vacuum chamber, a specimen holder, for holding a specimen in an irradiation position, a particle-optical column, for producing a charged-particle beam and directing it so as to irradiate the specimen. The method comprises introducing the specimen into the vacuum chamber, providing it on the specimen holder and maintaining it at a cryogenic temperature, employing at least one vacuum pump to evacuate the vacuum chamber, activating the beam, and directing it onto a portion of the specimen so as to modify a surface thereof. The disclosure also relates to a charged-particle microscope suitable for performing such a method.

The term "cryogenic" should be interpreted as referring to temperatures at or below −150° C. Such temperatures occur, for example, in cryogens (cryogenic fluids) such as liquid nitrogen, liquid ethane, liquid propane, liquid oxygen, and mixtures hereof.

The disclosed methods and apparatus can address this issue. More specifically, alternative approaches are provided that can be used to achieve both improved throughput and improved specimen quality when processing cryogenic specimens in a CPM.

This can be achieved in methods as characterized by the following steps: (i) providing a thin film monitor in the vacuum chamber and maintaining at least a detection surface thereof at a cryogenic temperature, (ii) using the monitor to measure a precipitation rate value of frozen condensate in the chamber, and (iii) using this value as a trigger to perform at least one of (re)-initiating surface modification, when the precipitation rate value falls below a first pre-defined threshold, or interrupting surface modification, if the value rises above a second pre-defined threshold.

The phrase "thin film monitor" is used here to indicate a device or arrangement that can be used to measure and monitor the thickness (change) of a thin film, e.g. during a deposition process. Such thin film monitors are, for example, employed in sputter coaters as a means of determining deposition thickness of intentionally sputtered material. However, their use in a CPM, their use at cryogenic temperatures so as to mimic the thermal conditions of a given specimen, their use to measure unintended condensate (ice) accumulation, and their use to determine an appropriate starting time for surface modification of a specimen with an actinic beam, are all new.

The disclosure has a number of pronounced advantages relative to the prior art. In particular, instead of the "blind" or "default" pumping period employed by the prior art after specimen loading, the present disclosure provides a quantitative way of tailoring the pumping period to each given situation. In this way, one can prevent unnecessary over-pumping (with its attendant throughput penalty) but can also avoid under-pumping (e.g. in a situation in which vapor condensation on the specimen is worse than foreseen). Instead, the disclosure allows an exactly determined, situation-specific pumping period to be employed on a case-by-case basis, whereby surface modification will only be initiated when the measured precipitation rate value falls below a pre-defined (first) threshold value.

Additionally, the disclosure provides a warning mechanism for an unexpected/undesired increase in precipitation rate during surface modification—e.g. caused by outgassing, or a leak in a Gas Injection System (GIS), for instance—allowing surface modification to be (temporarily) paused if a given (second) threshold value is exceeded. This second threshold value may be chosen to be equal to or different from the abovementioned first threshold value, as desired. If such processing interruption occurs, it can be resumed again if/when the measured precipitation rate value once again falls below said first threshold value.

The disclosure provides an innovative metric for the actual amount of condensate that has precipitated on a specimen surface during pump-down and prior to surface modification. Although this condensate will ultimately be locally removed when surface modification commences, its presence can affect the beam modification process (e.g. duration, required intensity, focus depth of the modifying beam, etc.); accordingly, being able to quantify the condensate thickness beforehand allows (various parameters of) the surface modification process to be more accurately tailored to the situation at hand, thereby serving to improve the accuracy and efficiency of the process.

It similarly provides a useful metric for an amount of condensate that may possibly precipitate on a specimen surface after termination of planned surface modification and before removal/lift-out, allowing the operator to resort to additional, corrective processing (e.g. extra precision polishing) as a supplement to the originally planned processing, thereby preventing a "dud"/reject specimen.

In a particular embodiment of the disclosure, the employed thin film monitor comprises a resonant crystal thickness monitor. A resonant crystal thickness monitor (resonant crystal microbalance) operates on the principle that the resonant frequency of a suitable crystal (e.g. quartz) will change measurably and reproducibly as a coating is deposited on the crystal. In this case, the "detection surface" referred to above is an integral (presented) surface of the resonant crystal upon which the frozen precipitate will accumulate.

In an alternative embodiment of the disclosure, the detection surface is comprised on a reference plate, and a measurement system is used to detect a change in an optical or electrical property of said plate as a result of accumulation of condensate thereon.

The reference plate may, for example, be a (smooth/polished) metal or ceramic plate or block that is cooled to a cryogenic temperature. The measurement system may, for example, comprise an ellipsometer, in which case a photonic beam will be directed onto and reflected from the reference plate in order to measure a change in optical properties of the accumulating precipitate film on the plate as time progresses, allowing changes in the film thickness (and, thus, the precipitation rate) to be derived. As an alternative, one could, for example, perform optical density measurements or magnetic induction measurements on the plate to achieve similar thickness change information. Yet another alternative is to use laser Doppler vibrometry on the plate. For more information on some of these techniques, see, for example, the WIKIPEDIA entries "Ellipsometry," and "Laser Doppler Vibrometer."

Although specific examples given above use a (focused) ion beam to perform surface modification on the specimen (ion beam milling), this is not the only type of surface modification that falls within the scope of the present disclosure. Other (non-limiting) examples include, for instance, ion beam induced etching (IBIE), electron beam induced etching (EBIE), ion beam induced deposition (IBID), electron beam induced deposition (EBID), and combinations hereof—in all of which a precursor gas is (locally) "activated" by a charged particle beam, so as to cause the gas to (locally) etch the specimen surface or to (locally) deposit a layer of material (such as an oxide, nitride, silicate, etc.) thereon. All such processes can be adversely affected by the (continuing) accumulation of condensate on the (freshly exposed or coated) specimen surface.

In an advantageous embodiment of the disclosure, the employed detection surface is movable and is configured to be retractable when not in use, and positioned proximal the specimen holder when in use.

The vicinity of the specimen holder in a CPM is generally an extremely cramped space, which is packed with instruments such as the specimen holder itself, terminal lens element(s), manipulator arms, detectors, etc. So, if one wants to be able to use the thin film monitor to take thickness measurements at a location that is close to the specimen (when on the holder), then it is of great advantage to be able to get the detection surface out of the way when it is no longer needed. This is inter alia because retracting the detection surface in this way will (i) free-up space around the specimen holder, allowing freer movement of tools (such as manipulator arms) in the vicinity of the holder, and (ii) get the detection surface out of the way of potentially harmful debris produced by the surface modification process when it commences (if so desired). One could, for example, mount the detection surface on an arm, sled, etc., that can be pulled/swung/hinged between a deployed position (which may be adjustable) and a parked position. It should, however, be realized that such retractability is purely optional: if desired/preferred, the (detection surface of the) thin film monitor may be in a fixed location.

As regards cooling the detection surface of the thin film monitor to a cryogenic temperature (and maintaining it at such a temperature), one way to achieve this is by providing said detection surface on a thermally conductive (e.g. metallic) frame comprising an appendage (such as a metal wick or rod, for example) that is immersed in a cryogen bath (in a dewar, flask, vat, etc.); this is sometimes referred to as a "cold finger" set-up. Alternatively, use can be made of a conduit through which coolant fluid is passed/pumped (such as liquid cryogen, or super-cooled nitrogen gas at a temperature just above its condensation point, for example). Since the specimen and specimen holder are often cooled using a similar set-up, an efficient approach is to mount (in a thermally conductive manner) said detection surface on a (peripheral) part of the specimen holder, so that a single cryogen bath can be used to concurrently cool each of the specimen holder, specimen, and detection surface. Note that the present disclosure does not require the detection surface and specimen to be at exactly the same temperature—although such a situation can be considered as ideal; instead, it suffices if both are below a temperature of −150° C., though their actual temperatures may mutually differ by several (tens of) degrees.

It should be noted that actions taken in response to a precipitation rate value supplied by the thin film monitor of the present disclosure may be fully automated (e.g. as executed by a pre-programmed computer processor), fully manual (e.g. instigated by a machine operator in response to a said value), or semi-automatic (a hybrid automatic/manual approach). The disclosure will now be elucidated in more detail on the basis of exemplary embodiments and the accompanying schematic drawings. In the Figures, where pertinent, corresponding parts are indicated using corresponding reference symbols. It should be noted that, in general, the Figures are not to scale.

DETAILED DESCRIPTION

Embodiment 1

Figure 1:
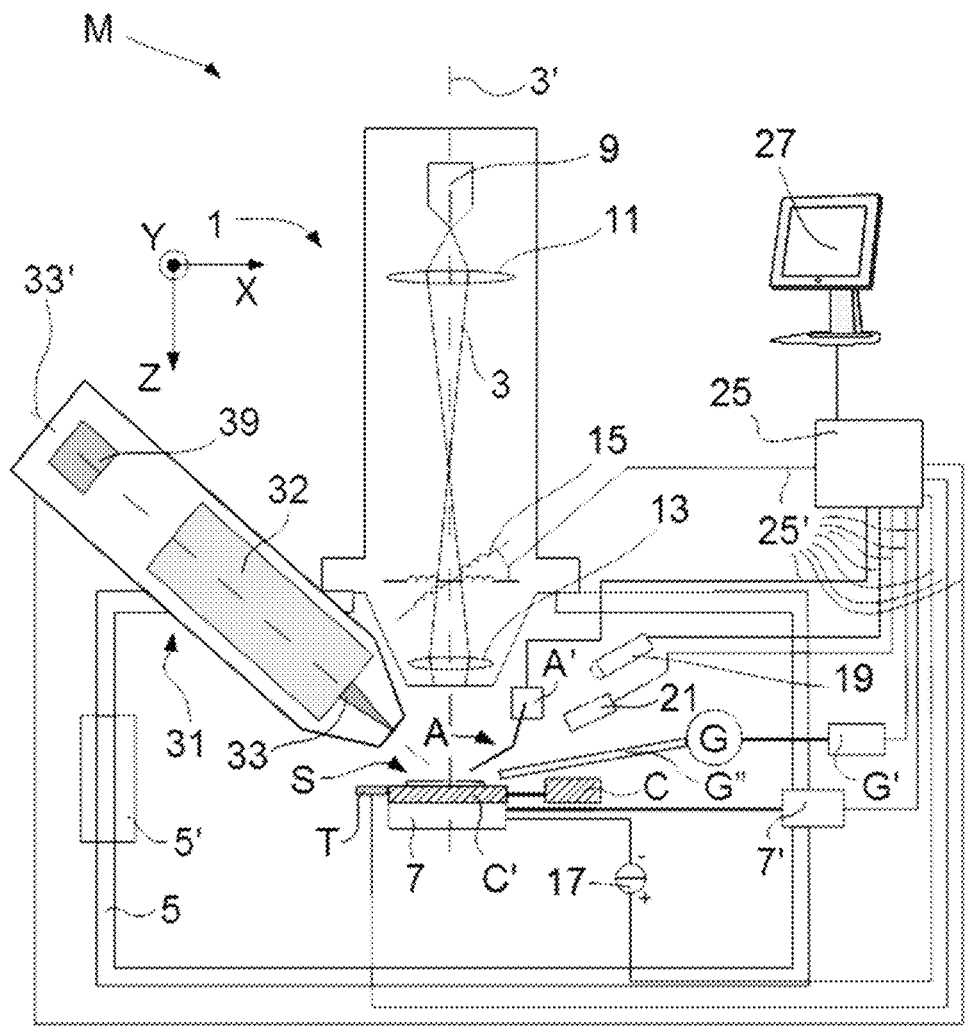
FIG. 1 renders a longitudinal cross-sectional view of an embodiment of a CPM in which the present disclosure is implemented.

FIG. 1 is a highly schematic depiction of an embodiment of a CPM in which the present disclosure is implemented. More specifically, it shows an embodiment of a microscope M, which, in this case, is a FIB-SEM (though, in the context of the current disclosure, it could just as validly be an ion-based microscope, for example). The microscope M comprises a particle-optical column (illuminator) 1, which produces a beam 3 of charged particles (in this case, an electron beam) that propagates along a particle-optical axis 3'. The column 1 is mounted on a vacuum chamber 5, which comprises a specimen holder 7 and associated actuator(s) 7' for holding/positioning a specimen S. The vacuum chamber 5 is evacuated using vacuum pumps (not depicted). With the aid of voltage supply 17, the specimen holder 7, or at least the specimen S, may, if desired, be biased (floated) to an electrical potential with respect to ground. Also depicted is a vacuum port 5', which may be opened so as to introduce/remove items (components, specimens) to/from the interior of vacuum chamber 5. A microscope M may comprise a plurality of such ports 5', if desired.

The column 1 (in the present case) comprises an electron source 9 (such as a Schottky gun, for example), lenses 11, 13 to focus the electron beam 3 onto the specimen S, and a deflection unit 15 (to perform beam steering/scanning of the beam 3). The microscope M further comprises a controller/computer processing apparatus 25 for controlling inter alia the deflection unit 15, lenses 11, 13 and detectors 19, 21, and displaying information gathered from the detectors 19, 21 on a display unit 27.

The detectors 19, 21 are chosen from a variety of possible detector types that can be used to examine different types of emergent radiation emanating from the specimen S in response to irradiation by the (impinging) beam 3. In the apparatus depicted here, the following (non-limiting) detector choices have been made: (i) detector 19 is a solid state detector (such as a photodiode) that is used to detect cathodoluminescence emanating from the specimen S. It could alternatively be an X-ray detector, such as Silicon Drift Detector (SDD) or Silicon Lithium (Si(Li)) detector, for example, and (ii) detector 21 is an electron detector in the form of a Solid State Photomultiplier (SSPM) or evacuated Photomultiplier Tube (PMT) [e.g. Everhart-Thornley detector], for example. This can be used to detect backscattered and/or secondary electrons emanating from the specimen S. The skilled artisan will understand that many different types of detector can be chosen in a set-up such as that depicted, including, for example, an annular/segmented detector.

By scanning the beam 3 over the specimen S, emergent radiation—comprising, for example, X-rays, infrared/visible/ultraviolet light, secondary electrons (SEs) and/or backscattered electrons (BSEs)—emanates from the specimen S. Since such emergent radiation is position-sensitive (due to said scanning motion), the information obtained from the detectors 19, 21 will also be position-dependent. This fact allows (for instance) the signal from detector 21 to be used to produce a BSE image of (part of) the specimen S, which image is basically a map of said signal as a function of scan-path position on the specimen S.

The signals from the detectors 19, 21 pass along control lines (buses) 25', are processed by the controller 25, and displayed on display unit 27. Such processing may include operations such as combining, integrating, subtracting, false colouring, edge enhancing, and other processing known to the skilled artisan. In addition, automated recognition processes (e.g. as used for particle analysis) may be included in such processing.

In addition to the electron column 1 described above, the microscope M also comprises an ion-optical column 31. In analogy to the electron column 1, the ion column 31 comprises an ion source 39 (such as a liquid metal ion source, for example) and imaging optics 32, and these produce/direct an ion beam 33 along an ion-optical axis 33'. To facilitate easy axis to specimen S on holder 7, the ion axis 33' is canted relative to the electron axis 3'. As hereabove described, such an ion (FIB) column 31 can be used to perform processing/machining operations on the specimen S, such as incising, milling, etching, depositing, etc.

As here depicted, the CPM M makes use of a manipulator arm A, which can be actuated in various degrees of freedom by actuator system A', and can (if desired) be used to assist in transferring specimens to/from the specimen holder 7, e.g. as in the case of a so-called TEM lamella excised from the specimen S using ion beam 33.

Also illustrated is a Gas Injection System (GIS) G, which can be used to effect localized injection of gases, such as etching or precursor gases, etc., for the purposes of performing gas-assisted etching or deposition. Such gases can be stored/buffered in a reservoir G', and can be administered through a narrow nozzle G", so as to emerge in the vicinity of the intersection of axes 3' and 33', for example.

Additional embodiments comprise the use of a controlled environment at the specimen S, e.g. maintaining a pressure of several mbar (as used in an Environmental SEM or low-pressure SEM).

In the context of the current disclosure, the specimen S is maintained at a cryogenic temperature using a cooling system C—e.g. using a cryogen vat or flowing coolant as set forth above, which will generally be in good thermal contact with (part of) the specimen holder 7; to that end, the Figure illustrates an exemplary situation in which a thermal sink C' (such as a metallic body/block) is thermally connected to a cooler C (e.g. a vat of (circulating) cryogenic fluid). Moreover, a thin film monitor T—which, in this case, is a resonant crystal thickness monitor (e.g. quartz crystal microbalance)—is present in the enclosure 5, and this too is maintained at a cryogenic temperature, preferably equal to or close to that of the specimen S; once again, this can be done using cooling means as set forth above, for example. In the present embodiment, the thickness monitor T is mounted on the specimen holder 7, and shares the cooling effect of cooling system C, C' (by being in intimate thermal contact with thermal sink C'); however, this does not have to be the case, and one could instead position the thickness monitor T elsewhere (preferably—but not necessarily—relatively near the intersection of axes 3' and 33'), either in a fixed or retractable position, and provide it with its own cooling system. The thickness monitor may, for example, be a commercially available quartz crystal microbalance, e.g. as supplied by RenLux Crystal, China.

There are various mechanisms by which vapor levels within the enclosure 5—and specifically in the vicinity of the specimen S—can attain unwanted levels. For example, (i) introduction or loading of a specimen S into the enclosure 5 or onto the specimen holder 7 can cause the unwanted proliferation of (water) vapor. Such introduction can occur via load port 5', or from an antechamber/in situ cassette, for example, (ii) there may be a leak out of the GIS G, (iii) some component within the enclosure 5 may be outgassing, or (iv) some other mechanism could cause unwanted vapor levels.

Such vapor can be a nuisance if it precipitates and congeals upon surfaces of the cooled specimen S—particularly surfaces that have just been freshly created/exposed by milling/etching with ion beam 33, for example. In accordance with the disclosure, the thin film monitor T provides a means of quantitatively monitoring the precipitation rate of vapor condensate in the vicinity of the specimen S, allowing an informed decision as to when it is prudent to commence/interrupt/re-do component steps of a surface modification procedure (e.g. as part of a TEM lamella creation and extraction routine).

Embodiment 2

Figure 2:
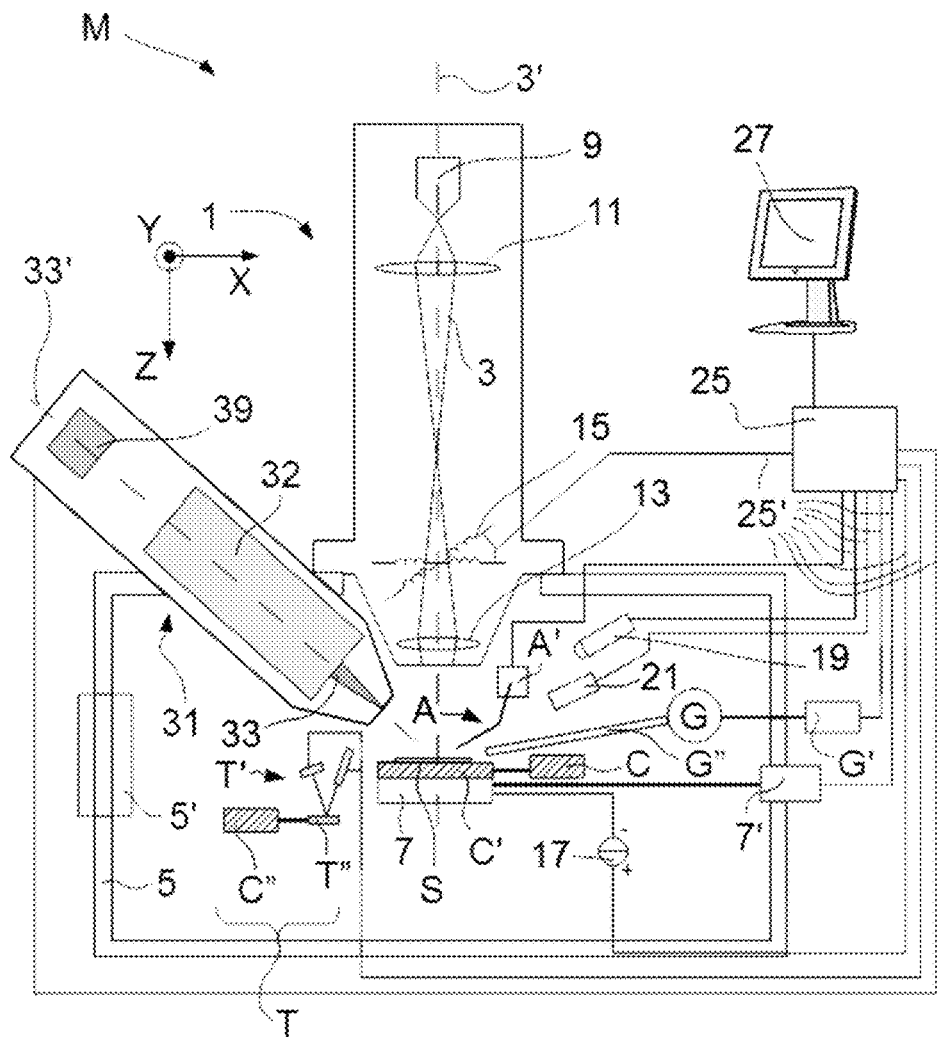
FIG. 2 shows an alternative embodiment to that of FIG. 1.

FIG. 2 is identical in most respects to FIG. 1, except as regards details of the employed thin film monitor T. In the current instance, the thin film monitor T is embodied such that (i) it is no longer mounted on the specimen holder 7, (ii) it has it's own cryogenic cooling system C", and (iii) it comprises a separate reference plate T" and measurement system T'. For example, the measurement system T' may employ a laser beam that is reflected off a polished surface of plate T" and into a detector, and which uses ellipsometry to derive the accumulation rate of precipitate on plate T" (and, by inference, on specimen S).

In view of the many possible embodiments to which the principles of the disclosure may be applied, it should be recognized that the illustrated embodiments are only preferred examples and should not be taken as limiting the scope of the disclosure. We claim all that comes within the scope and spirit of the appended claims.

We claim:

1. A method comprising:
   directing a charged-particle beam onto a portion of a specimen, situated in a vacuum chamber and maintained at a cryogenic temperature so as to perform a surface modification thereof;
   providing a thin film monitor in the vacuum chamber and maintaining at least a detection surface thereof at a cryogenic temperature; and
   using the thin film monitor to measure a precipitation rate of frozen condensate in the vacuum chamber,
   wherein when either the precipitation rate falls below a first pre-defined threshold, the surface modification is initiated, or when the precipitation rate rises above a second pre-defined threshold, the surface modification is interrupted, or both.

2. The method of claim 1, wherein the thin film monitor comprises a resonant crystal thickness monitor.

3. The method of claim 2, wherein the detection surface is movable and is configured to be retractable when not in use and wherein the detection surface is positioned proximal a specimen holder when in use.

4. The method of claim 2, wherein the surface modification is produced by ion beam milling, ion beam induced etching (IBIE), electron beam induced etching (EBIE), ion beam induced deposition (IBID), electron beam induced deposition (EBID), or combinations thereof.

5. The method of claim 2, wherein the detection surface is maintained at a cryogenic temperature using at least one of the following techniques: (i) providing the detection surface on a thermally conductive frame comprising an appendage that is immersed in a cryogen bath; (ii) disposing the detection surface in thermal contact with a conduit through which a coolant fluid is passed.

6. The method of claim 1, wherein the detection surface comprises a reference plate, and wherein a measurement system is used to detect a change in an optical or electrical property of the reference plate as a result of accumulation of condensate thereon.

7. The method of claim 6, wherein the measurement system comprises an ellipsometer.

8. The method of claim 6, wherein the surface modification is produced by ion beam milling, ion beam induced etching (IBIE), electron beam induced etching (EBIE), ion beam induced deposition (IBID), electron beam induced deposition (EBID), or combinations thereof.

9. The method of claim 6, wherein the detection surface is maintained at a cryogenic temperature using at least one of the following techniques: (i) providing the detection surface on a thermally conductive frame comprising an appendage that is immersed in a cryogen bath; (ii) disposing the detection surface in thermal contact with a conduit through which a coolant fluid is passed.

10. The method of claim 1, wherein the surface modification is produced by ion beam milling, ion beam induced etching (IBIE), electron beam induced etching (EBIE), ion beam induced deposition (IBID), electron beam induced deposition (EBID), or combinations thereof.

11. The method of claim 10, wherein the detection surface is maintained at a cryogenic temperature using at least one of the following techniques: (i) providing the detection surface on a thermally conductive frame comprising an appendage that is immersed in a cryogen bath; (ii) disposing the detection surface in thermal contact with a conduit through which a coolant fluid is passed.

12. The method of claim 1, wherein the detection surface is movable and is configured to be retractable when not in use and wherein the detection surface is positioned proximal the specimen holder when in use.

13. The method of claim 12, wherein the detection surface is maintained at a cryogenic temperature using at least one of the following techniques: (i) providing the detection surface on a thermally conductive frame comprising an appendage that is immersed in a cryogen bath; (ii) disposing the detection surface in thermal contact with a conduit through which a coolant fluid is passed.

14. The method of claim 1, wherein the detection surface is maintained at a cryogenic temperature using at least one of the following techniques: (i) providing the detection surface on a thermally conductive frame comprising an appendage that is immersed in a cryogen bath; (ii) disposing the detection surface in thermal contact with a conduit through which a coolant fluid is passed.

15. The method of claim 1, wherein the detection surface is mounted on part of a specimen holder.

16. The method of claim 1, further comprising producing an electron beam and directing the electron beam so as to irradiate the specimen, and producing an ion beam and directing the ion beam so as to irradiate the specimen, wherein one of the electron beam and the ion beam is used to image the specimen, and the other of the electron beam and the ion beam is used to perform the surface modification.

17. A charged particle microscope, comprising:
   a vacuum chamber that includes a port for loading a specimen into the vacuum chamber;
   a specimen holder for holding the specimen in an irradiation position and maintaining the specimen at a cryogenic temperature;
   a particle-optical column situated to produce a charged-particle beam and direct the charged-particle beam so as to irradiate the specimen;

a thin film monitor situated in the vacuum chamber and thermally coupled to a cooling device so as to maintain at least a detection surface of the thin film monitor at a cryogenic temperature; and a controller coupled to the particle-optical column and the thin film monitor so as to measure a precipitation rate of frozen condensate in the vacuum chamber, wherein when the precipitation rate falls below a first pre-defined threshold, the controller initiates irradiation of the specimen by the charged-particle beam, and when the precipitation rate rises above a second pre-defined threshold, the controller interrupts irradiation of the specimen by the charged-particle beam.

18. The charged particle microscope of claim 17, wherein the thin film monitor comprises a resonant crystal thickness monitor.

19. The charged-particle microscope of claim 17, wherein the detection surface is mounted on part of the specimen holder.

20. The charged-particle microscope of claim 17, wherein the detection surface is movable and is configured to be retractable when not in use and positioned proximal the specimen holder when in use.

* * * * *